United States Patent
Grangeat et al.

[19]

[11] Patent Number: 5,933,517
[45] Date of Patent: Aug. 3, 1999

[54] INSTALLATION AND PROCESS FOR THE RECONSTRUCTION OF THREE-DIMENSIONAL IMAGES

[75] Inventors: Pierre Grangeat, Saint Ismier; Régis Guillemaud, Grenoble, both of France

[73] Assignee: Commissariat a l'Energie Atomique, Paris, France

[21] Appl. No.: 08/797,266

[22] Filed: Feb. 7, 1997

Related U.S. Application Data

[63] Continuation of application No. 08/249,993, May 27, 1994, abandoned.

[30] Foreign Application Priority Data

Jun. 2, 1993 [FR] France ................................. 93 06564

[51] Int. Cl.⁶ ....................................................... G06K 9/00
[52] U.S. Cl. ........................ 382/131; 382/276; 250/363.1
[58] Field of Search ................................... 382/131, 276; 250/363.1

[56] References Cited

U.S. PATENT DOCUMENTS

| | | | |
|---|---|---|---|
| 4,820,924 | 4/1989 | Hsieh | 250/363.1 |
| 4,823,017 | 4/1989 | Hsieh | 250/363.1 |
| 4,868,747 | 9/1989 | Mori et al. | 382/131 |
| 4,894,776 | 1/1990 | Dekel | 382/131 |
| 5,150,427 | 9/1992 | Frazee et al. | 382/131 |
| 5,170,439 | 12/1992 | Zeng et al. | 382/131 |
| 5,333,107 | 7/1994 | Grangeat et al. | 364/413.19 |
| 5,402,337 | 3/1995 | Nishide | 382/131 |
| 5,404,293 | 4/1995 | Weng et al. | 382/131 |
| 5,444,792 | 8/1995 | Grangeat et al. | 382/276 |

FOREIGN PATENT DOCUMENTS 0 526 970 2/1993 European Pat. Off. ........ G06F 15/62

OTHER PUBLICATIONS

Ogawa et al., "A Reconstruction Algorithm from Truncated Projections", IEEE Transactions on Medical Imaging, vol. M1–3, No. 1, Mar. 1984, pp. 34–40.

Kudo, et al; "Three–Dimensional Helical–Scan Computed Tomography Using Cone–Beam Projections", *Systems and Computers in Japan*, vol. 23, No. 12, pp. 75–82, 1992, USA.

Zeng, et al; "Three–Dimensional Iterative Reconstruction Algorithms With Attenuation and Geometric Point Response Correction", *IEEE Transactions on Nuclear Science*, vol. 38, No. 2, pp. 693–701, Apr. 1991, USA.

Grangeat, et al; "Recents Evolutions De La Tomographie 3D En Geometrie Conique", *Trezième Collogue Sur Le Traitement Du Signal Et Des Images*, pp. 817–820, Sep. 16, 1991, France.

*Primary Examiner*—Jose L. Couso
*Assistant Examiner*—Anh Hong Do
*Attorney, Agent, or Firm*—Burns, Doane, Swecker & Mathis LLP

[57] ABSTRACT

Apparatus and process for obtaining three-dimensional images of an object by a planar array of detectors, whose focusing points are located on a circle. The advantage obtained is a wider detection field that in the case of focusing on a single point. Rules are given for using algorithms for inverting characteristic measurements of the conical focusing. Application to medicine and to non-destructive testing in industry.

5 Claims, 3 Drawing Sheets

INSTALLATION AND PROCESS FOR THE RECONSTRUCTION OF THREE-DIMENSIONAL IMAGES

This application is a continuation of application Ser. No. 08/249,993, filed May 27, 1994, now abandoned.

BACKGROUND OF THE INVENTION

1. Field of the Invention

The invention relates to an installation and a process for the reconstruction of three-dimensional images.

2. Description of the Prior Art

The objects whereof it is wished to reconstruct the image by a tomography process, particularly in medicine or non-destructive testing in industry, are placed in front of a two-dimensional array of sensors rotating about them. The array is covered with a collimator, i.e. a plate made from lead or a similar material, which limits the space scanned by each detector to a single line. The array is passed over a circle or another closed trajectory about the object or a helical trajectory, and the collation of the measurements of the detectors, collected for several bidimensional images taken with the same number of different incidences, makes it possible to reconstruct a three-dimensional image of the object by using an analytical method for inverting a mathematical transform of the measurements or an algebraic resolution for inverting a system of equations. The function of the object or the property characterizing the image and which is measured by the detectors is either the emission of a radiation by the points of the object, or the attenuation by the points of the object of a radiation emitted by a source beyond the object on the focusing lines.

The location of the focusing points of the detectors, i.e. intersection points of the focusing lines, can assume different forms. It has thus been proposed to use a purely conical collimation, where there is a single focusing point for each two-dimensional image, which makes it possible to only use a point source. Earlier works carried out by one of the inventors and by other scientists have proved the value of this solution when using the inversion of what is called the primary of highest derivative of the Radon transform of the function in order to reconstitute the images, particularly in European patent 292 402, or more generally the sums of the function on planes.

It has also been proposed to focus the detectors on a straight line parallel to the rotation axis of the array, i.e. the focusing lines are arranged in fan form on staged planes and parallel to the trajectory. This "parallel fan" focusing mode, described in a certain number of articles, is disadvantageous due to the absence of magnification in the rotation axis.

More complex focusing locations are proposed in U.S. Pat Nos. 4,820,924 and 4,823,017. The collimating lines of the horizontal and vertical rows (rows and columns) of detectors converge in at least certain cases on the lines perpendicular to the array. In one embodiment, the focusing location is a straight line parallel to the array and perpendicular to the rotation axis. However, then the reconstruction calculation become very complicated.

The article by Müller, Arce and Blake entitled "Truncation artifacts and synthetic scanner arrays in two-dimensional computerized tomography", published in the reports of ECAPT, Karlsruhe, 1993 describes a method for the reconstruction of three-dimensional images, which comprises a stage of converting the projections into virtual projections in order to reduce the effects of the truncation of the measurements. The array of detectors makes it possible to acquire a plurality of truncated projections in conical geometry, as a result of the circular movement of the detector array and which is independent of that of the source and the virtual projections take place on a planar, virtual array of sensors. The invention also involves a conversion of real projections into virtual projections, but under different acquisition conditions, because the focusing is conical or in parallel fans in said article.

SUMMARY OF THE INVENTION

The invention relates to an installation, whose focusing point is not punctiform, but which still makes it possible to use with few adaptations the image reconstruction algorithms associated with purely conical focusing, unlike in the case of parallel fan focusing which requires completely different processing operations.

A defect inherent in punctiform or point focusing is that the examination field very rapidly narrows towards the focus. If this point is relatively close to the object, part of the latter is not generally included in the radiation field of all the measurements and then truncated measurements are obtained, which give rise to reconstruction errors which cannot be corrected in inversion formulas. If the focal point is spaced from the object or if the object is close to the detector array, it is usually entirely included in the examination cone, but the image magnification is weaker, which is regrettable if there is an interest in examining part of the object, such as an organ in the human body, because most detectors are used for measurements relating to other parts of the object.

In summarizing, the invention relates to an installation for the reconstruction of three-dimensional images of an object, comprising a two-dimensional array of detectors oriented towards the object, the detector array being mobile about the object rotating about an axis along a helical trajectory, being characterized in that the detectors are focused, in an axial direction, onto a plurality of points substantially located on a helix centred on the axis, and per se known means for storing the measurements performed by the detectors and for combining the measurements are used for reconstructing the images. The expression combining the images means a series of stages such as e.g. rearrangements and processing of the measurements and the three-dimensional image reconstruction processes. The examination prism is then much wider than a cone. It is possible that the trajectory is circular and the helix is a circle, which corresponds to a zero helix pitch. This is very important, because equipments are generally designed for realizing such trajectories, but does not in reality differ from the general case for the reconstruction process and the calculations.

The detectors of the array located on a column parallel to the axis are preferably all focused on a single point from among the focusing points, in order to facilitate the calculations.

The invention also relates to the process offering the possibility of making use of measurements performed in particular with the installation defined hereinbefore by converting them into characteristic data of a purely conical focusing, which will be called virtual focusing. This conversion does not relate to the actual measurement values, but instead to the geometrical parameters which define them. In its most general form, the invention then relates to a process for the reconstruction of three-dimensional images of an object consisting of taking two-dimensional images of the object by at least one two-dimensional array of detectors mobile about the object turning around an axis following a helical trajectory, the two-dimensional images being constituted by measurement points for each of the detectors of a property along the collimating lines, the three-dimensional images being reconstructed by a method for resolving equations using the measurements, characterized in that each of the collimating lines passes substantially over a helix centred on the axis and that the process involves, prior to the resolution method, a conversion calculation stage of the parametrizing of the collimating lines, where each of the latter is assumed to be the origin of a virtual two-dimensional array of detectors focused onto a single focal point of the helix, the virtual array rotating about the axis and at a constant distance therefrom, the conversion calculations consisting of determining for each of the collimating lines of the virtual array, the position in the real array whereof it is the origin and the angular position of the real array about the axis, followed by a stage of regrouping the measurements in accordance with the determinations of the conversion calculations, so as to obtain virtual conical projections, the resolution relating to the regrouped measurements. The method of resolving the measurements advantageously incorporates an inversion of the primary derivative of the Radon transform of the function characterizing the image of the object.

For the sharpness of the image obtained, it is preferable for all the focusing lines to pass through the helix or optionally the circle, but this condition is not obligatory, because the deterioration of the image is only slightly sensitive if the said lines are slightly removed from the circle. Satisfactory results have been obtained if all the focusing lines pass through a straight line tangential to a circle, in accordance with the known collimators.

The pitch of the focusing helix can be identical to that of the trajectory, although this is not necessary.

BRIEF DESCRIPTION OF THE DRAWINGS

The invention is described in greater detail hereinafter relative to non-limitative embodiments and the attached drawings, wherein show.

DESCRIPTION OF THE PREFERRED EMBODIMENTS

Figure 1:
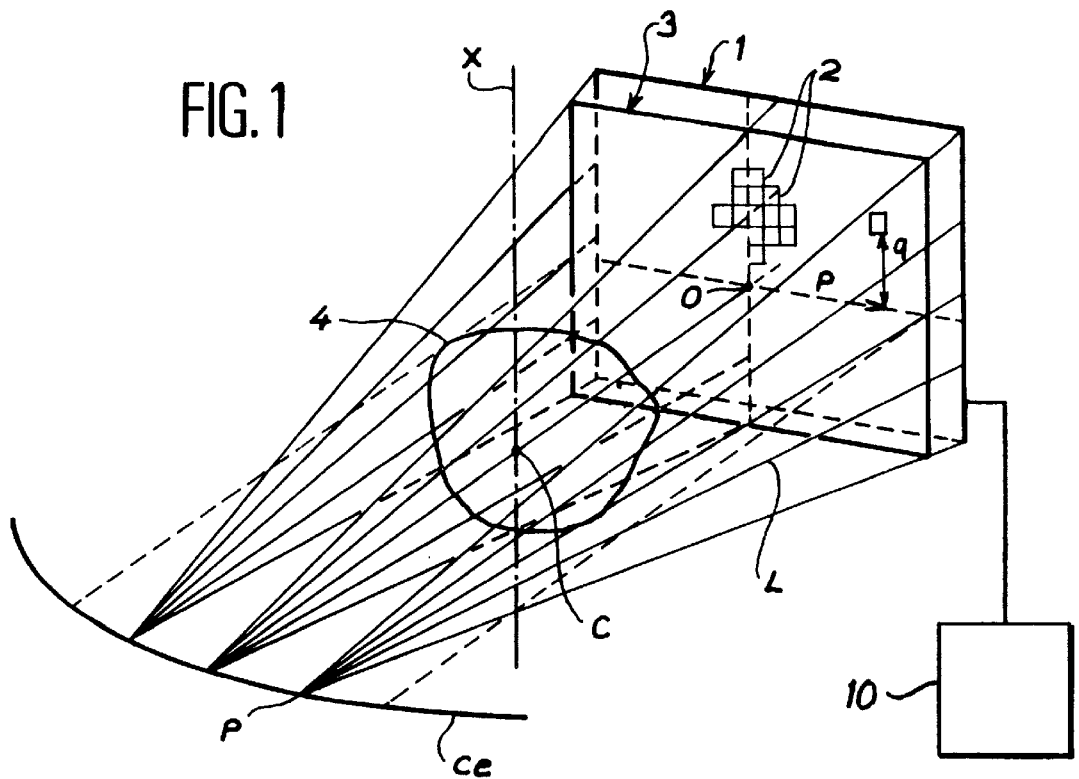
FIG. 1 A general, diagrammatic view of the invention.

FIG. 1 shows the array 1 of detectors 2, which are aligned on rows perpendicular to the rotation axis and columns parallel to the rotation axis and which can be identified by their row and column coordinates p and q in the plane of the array 1, starting from the centre 0 of the array 1.

A collimator 3 covers the array 1. It is not illustrated in detail, but in conventional manner comprises a plurality of windows made in a material opaque to the radiation to be measured by the detectors 2. Lead is generally used. The number of windows is equal to or greater than that of the detectors 2 and placed in front of each of them in order to enable them to scan the space on a focusing line L oriented towards the object 4 to be examined and beyond it. Advantageously, the collimator comprises a number of windows exceeding the number of detectors. Advantageously, the windows are of the same size and distributed homogeneously over the collimator surface.

The windows placed in front of a detector have adjacent perforation directions, so as to enable the detectors to scan the space on a single focusing line L. The direction of the line l is a mean direction of the directions of the windows in front of the detector.

The rotation axis of the array 1 is called X. The essential characterization of the invention consists of all the focusing lines L leading to a circle Ce positioned around the object 4 and which belongs to a plane perpendicular to the axis X, which advantageously passes through the centre C of the circle Ce. In the case of a helical trajectory, all the focusing lines L lead to a helix arc. This plane is called the focusing plane. Moreover, the focusing lines L of all the detectors 2 located on each column converge towards a respective single point P. It is immediately apparent that this arrangement of the focusing points P significantly widens the field of the space scanned and that the object 4 is much more easily included there, although the contribution of its points to the attenuation or emission of the radiation is more equitably measured. A collimator permitting such as arrangement of the focusing lines is called a multifocal geometry or multifocal collimator. Such a collimator can replace the parallel or conical collimators used on existing tomographs.

Figure 2:
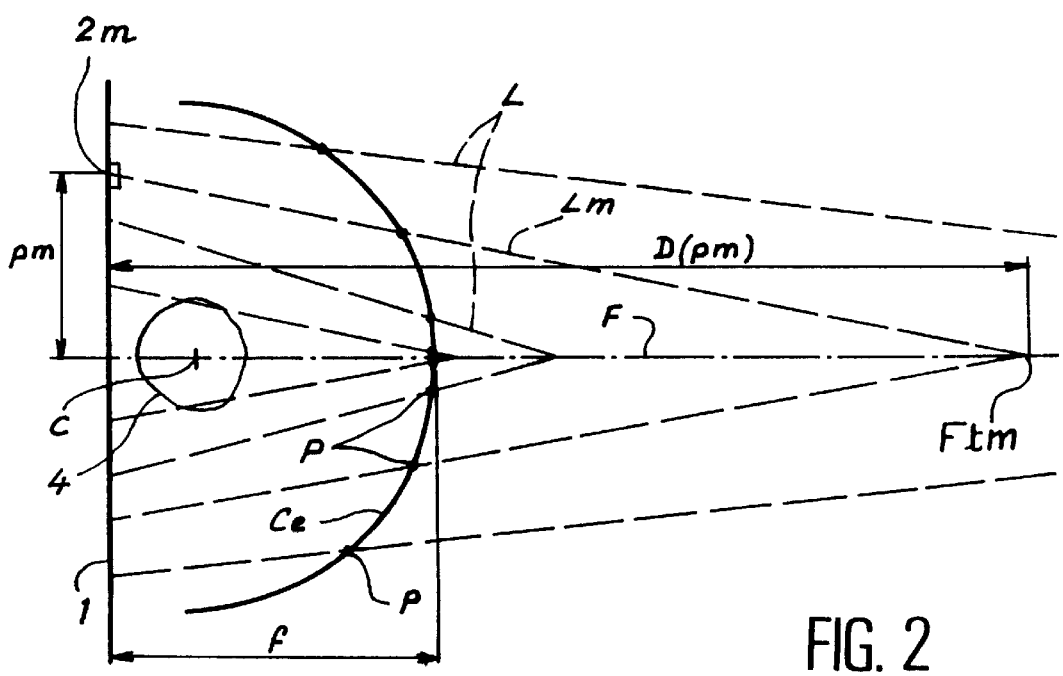
FIG. 2 The distribution of the focusing lines in a preferred embodiment viewed along the axis.

FIG. 2 is an orthogonal projection of the array 1 and the focusing lines L on he focusing plane. If F is the focal axis, i.e. the diametral axis of the circle Ce passing through the axis X and the centre 0 of the array 1, then f is the distance measured on the focal axis F between the circle Ce and the array 1, the projections of the focusing lines Lm in the focusing plane intersect the focal axis F at a plurality of transverse focal points Ftm. On considering a focusing line Lm, it is advantageous that, if the row coordinate of said detector 2m is pm, the transverse focal distance D(pm) between the transverse focal point Ftm and the array 1 is defined by a quadratic equation according to pm or at least increasing and exceeding f, i.e. according to equation (1)

$$D(pm)=f+k.pm^2 \qquad (1)$$

in which k is a constant coefficient.

Thus, a good compromise is then obtained between the need of covering the entire width of the object 4, which is brought about by external focusing lines L, which are only slightly convergent, and the frequent interest of obtaining a better resolution and sensitivity for the centre of the object 4, which is achieved by means of central focusing lines L, which converge to a much greater extent.

On returning again to FIG. 1, it is clear that a series of measurements by the array 1 around the axis X and the object 4 will supply a large number of measurements by the detectors 2 and it will be possible to arrange them so as to reconstruct the three-dimensional image of the object 4 in accordance with a method identical to that already in existence for conical focusing.

Figure 3:
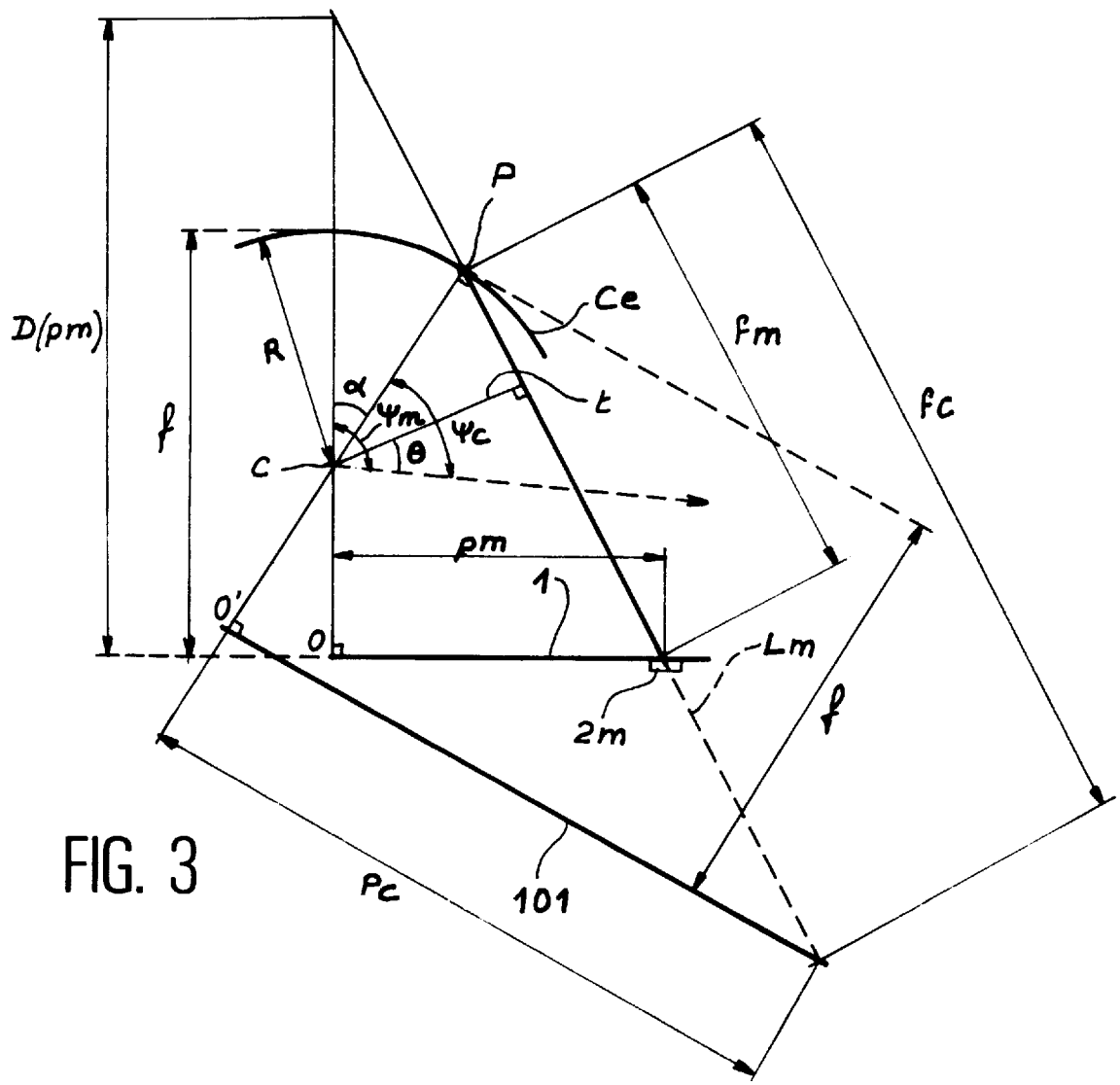
FIGS. 3 & 4 The method used for the reconstruction of images on the basis of a conical focusing.

This is effectively brought about by reducing all the measurements to those carried out with a purely conical, virtual focusing. FIG. 3 shows for one position of the array 1, the focusing line Lm of a detector 2m oriented towards a focusing point P. The distance from the array 1 to the circle Ce, whose radius is R, is once again designated f. On imagining a virtual detector array 101 with conical focusing, all these detectors converge towards the point P and on also choosing a distance f from the point P and the line passing through P and C perpendicular to the virtual array 101, then the latter is present in single form. The focusing line Lm is extended up to it, at a distance pc along the axis of the rows and qc along the axis of the columns from its centre 0's, defined as the orthogonal projection of the point P on the virtual array 101. The angle formed by the two arrays 1 an 101 is (pm).

It is then sufficient to find the relations between pc and pm, qc and qm, qm being the column coordinates of the detector 2m along the other coordinate of the arrays 1 and 101 (FIG. 4), as well as the angle (pm) for converting the measurements performed by the array 1 into measurements performed by the virtual array 101 and apply a known inversion algorithm like those using the primary derivative of the Radon transform. The existence of like triangles leads to the equation $$t = pc \frac{R}{\sqrt{f^2 + pc^2}} \quad (2)$$

in which t is the distance between the centre C and the line Lm and if $\psi m$ and $\psi c$ are used for designating the orientations of the arrays 1 and 101 with respect to the fixed reference axis of the focusing plane, the equation:

$$\odot = \psi c - arctg \frac{f}{pc} \quad (3)$$

in which $\odot$ designates the angle between the reference axis and the projection of the centre of the circle Ce on the focusing line Lm, can be defined. On introducing the distance D(pm), the equations (2) and (3) are equivalent to the equations (4) and (5):

$$t = pm \frac{D(pm) - (f - R)}{\sqrt{D(pm)^2 + pm^2}} \quad (4)$$

$$\odot = \psi m - arctg \frac{D(pm)}{pm} \quad (5)$$

On the basis of (2) and (4), the relation between pm and pc is obtained:

$$pm \frac{D(pm) - (f - R)}{\sqrt{D(pm)^2 + pm^2}} = pc \frac{R}{\sqrt{f^2 + pc^2}}$$

pm is then calculated as a function of pc.

It is possible to define a preestablished correspondence table.

On the basis of the equations (3) and (5), we obtain:

$$\psi m = \psi c - arctg \frac{f}{pc} + arctg \frac{D(pm)}{pm}$$

$$arctg \frac{D(pm)}{pm} - arctg \frac{f}{pc} = \delta\psi(pc).$$

It is possible to establish a correspondence table $\delta\psi$.

The variable change between $\psi m$ and $\psi c$ is defined by using the function $\delta\psi(pc)$ in the following way:

$$\psi m = \psi c + \delta\psi(pc)$$

Figure 4:
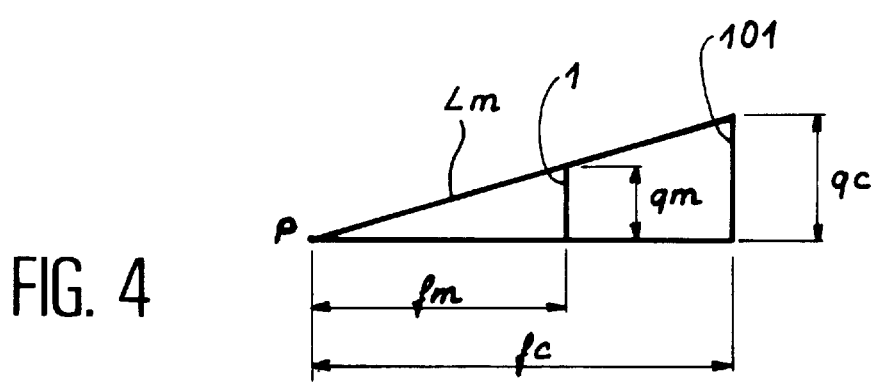

FIG. 4 immediately shows that qc/qm=fc/fm (6), in which fc and fm designate the length of the projections of the focusing line Lm on the focusing plane between the point P and, respectively, the real array 1 and the virtual array 101, fm and fc are given by the equations (7) and (8):

$$fm = (pm - R\sin\alpha(pm))\sqrt{1 + \left(\frac{D(pm)}{pm}\right)^2} \quad (7)$$

$$fc = \sqrt{f^2 + pc^2} \quad (8)$$

A correspondence table $\delta q$ is established. The change of variable between qm and qc is established by using the function $\delta q(pc)$ such that $qm = qc \times \delta q(pc)$ and $\delta q(pc) = fc/fm$: qm thus being obtained as a function of qc. In practice, for each point of the volume of virtual measurements $\psi c$, pc, qc, the coordinates of the volume of real measurements $\psi m$, pm, qm corresponding thereto, and resulting from the above equations are not integral, i.e. they do not correspond to measuring points. The determination of the value of the volume of real measurements at point c, pc and qc is brought about by trilinear interpolations or series of three successive linear interpolations at one dimension, all of which are dependent on D(pm), the helix pitch, the focal distance f, the distance between thee detector and the rotation axis R and, respectively, pm, $\psi m$ and qm. The real measurements are then associated with virtual measurements performed by the virtual array 101 moving around the object 4 and characterized by $\psi c$, pc and qc. These virtual measurements are combined, transformed and inverted by a process like that of EP-A-292 402, in which a brief description is also given of the essentially data processing, measurement storage means for implementing combinations for carrying out the inversion of the primary derivative of the Radon transform of the function and display the results. The measurement acquisition, combining/regrouping, storing, reconstructing and displaying means carry the general reference number 10 in FIG. 1.

In practice, use is made of the above formulas or any other group of formulas making it possible to pass from multifocal real measurements to conical virtual measurements. It is in all cases necessary to know D(pm) and it is possible to establish beforehand a tabulation of D(pm) as a function of pm, on the basis of immutable geometrical characteristics of the focusing illustrated in FIGS. 1 and 2. Seeking pm from pc and D(pm), which is specifically dependent on pm, is not always immediate and it is therefore preferable to establish beforehand the table of pm, $\delta\psi$ and $\delta q$ as a function of pc, rather than repeating the calculations for each of the measurements. In practice, said tables being established for an object to be reconstructed of dimension $N^3$, the rearrangement stage requires approximately $N^3$ trilinear interpolations, whereas the reconstruction stage requires approximately N elementary operations as described in EP-A-292 402.

The tables pm, $\delta\psi$ and $\delta q$ will be subsequently usable for the change of variables pm, qm, $\psi m$ as a function of pc, qc and $\psi c$ in the stage of converting real, multifocal measurements into virtual, conical measurements.

However, the complication to the process as caused by these conversions is not very sensitive and is generally less important than the better image obtained in numerous applications.

A specific device can comprise a collimator covering a rectangular detector array with a width of 450 mm and a height of 350 mm (in the direction of the axis X). It makes it possible to respect the situation of FIG. 2 and the equation (1) with k=0.016. As R=350 mm and f=600 mm, D(pm) varies from 600 to 1410 mm. The detector array belongs to a gamma camera making it possible to obtain acquisitions rotating about the patient (e.g. such a device is obtained from the mechanical part of the Sopha Medical DSX camera).

To bring about acquisitions in accordance with a helical trajectory, application also takes place, in addition to the rotary movement of the detector array, of a translatory movement on the part of the patient along the rotation axis. In order to simplify the description of the invention, the equations are given hereinafter, for measurements acquired by a planar detector. Nevertheless, a circular detector can be used and in this case determination occurs of the distribution of the acquisition line on the plane defined by the line connecting the two ends of the detector and its width.

The image reconstruction algorithm is advantageously an inversion of the primary derivative of the Radon transform, called the Grangeat algorithm, as has already been stated.

Figure 5:
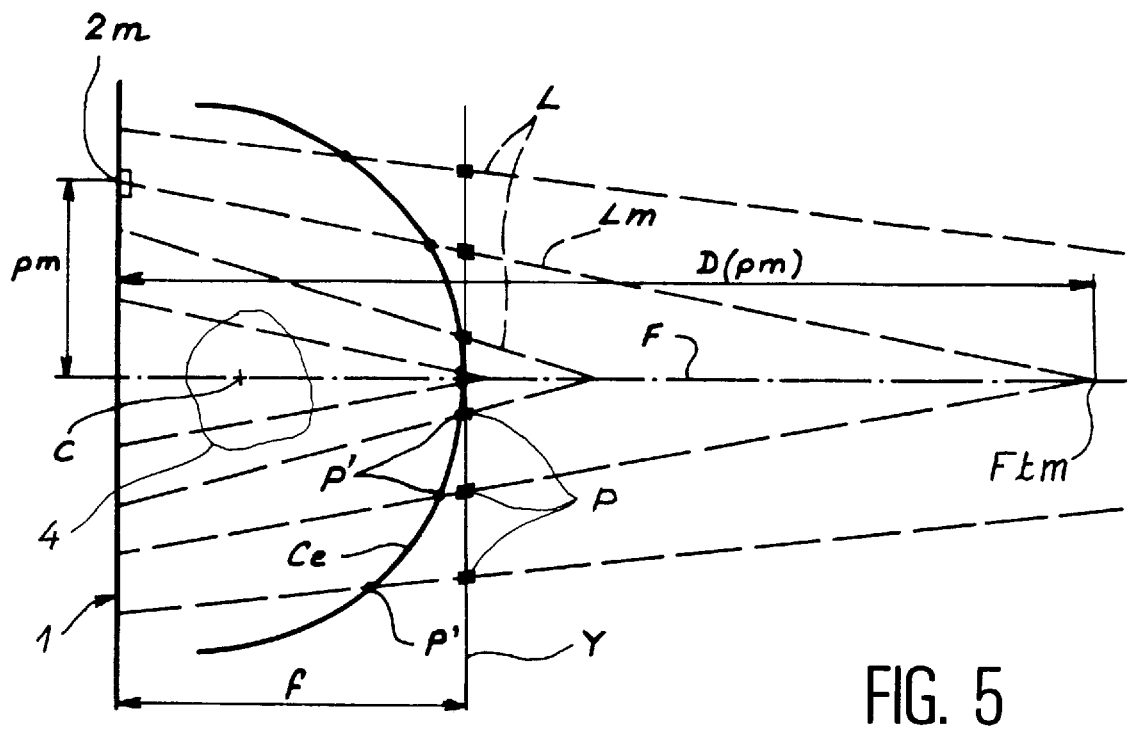
FIG. 5 How the invention can be used under conditions slightly differing from focusing on a circle.

If the focusing points P are advantageously located on a circle Ce of centre C belonging to the rotation axis X of the array 1, said condition is not obligatory, because the variations lead to a deterioration of the sharpness of the image which is generally of an acceptable quality. Thus, the focusing points can be located on a circle, whose centre does not coincide with the rotation axis X, but is close to it, which is due to the position and fitting uncertainties of the array 1 in the remainder of the apparatus. A different situation is referred to in FIG. 5, similar to FIG. 2, but where the focusing points P are placed on a line Y parallel to the array 1 and perpendicular to the axis X. An approximation is made by assuming that the focusing points P are located on a circle, e.g. on circle Ce. The points obtained under these conditions are projected and referenced by P'. The specifically correspond to the intersection of the circle Ce and the projection parallel to the axis X on the plane of the circle Ce of each of the focusing lines L. The focusing points P virtually coincide with the projected points P' at the centre of the image, so that the reconstructed three-dimensional image will be sharper for this region covering the object 4 than at the periphery of the image.

The described process can be completed by preliminary treatments, such as corrections of the uniformity and sensitivity of the detectors 2, as well as attenuation correction operations. This process can be used in conventional reconstructions and which are illustrated in the book "Physics in nuclear medicine" by J. A. Sorenson and M. E. Phelps, published by Saunders.

Figure 6:
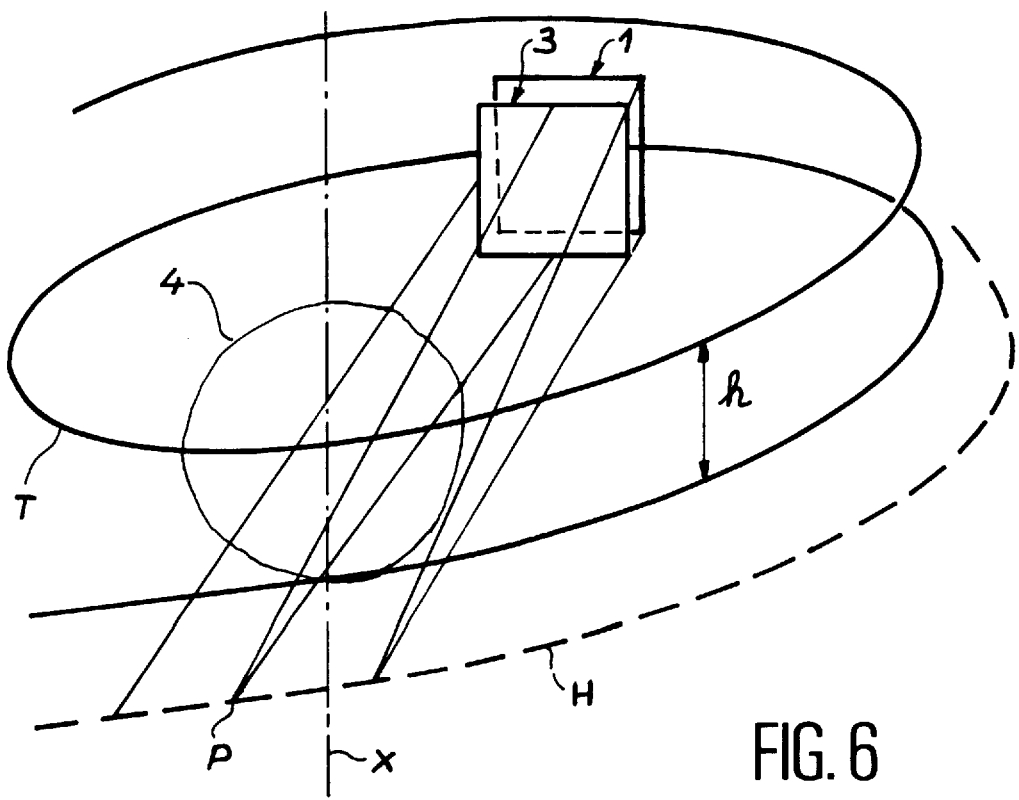
FIG. 6 A generalization of the method.

Explanations have already been given for the simplest case. The invention can be generalized to helical trajectories, where the detector array rises gradually around the object 4, which is shown in FIG. 6 where the trajectory T is a helix of pitch h between its turns. This helix is centred on the axis X. The location of the focusing points P of the collimator 3 then describes another helix of the same pitch h, which is designated H and whereof a portion is shown, said helix also being centred on the axis X. It is obvious that the reconstruction method remains the same, because each focusing point P can still be associated with detectors 2 of different columns. The pitch h only has an influence at the end of the calculations, for the reconstruction of the image as a function of the instant of each exposure. The circular trajectory and the circle Ce correspond to a zero helix pitch.

We claim:

1. Process for the reconstruction of three-dimensional images of an object consisting of taking two-dimensional images of the object by at least one two-dimensional array of detectors mobile about the object turning around an axis following a helical trajectory, the two-dimensional images being constituted by measurement points for each of the detectors of a property of the object along collimating lines focused on focusing points, the focusing point for the detectors along each of the collimating lines forming a plurality of focusing points at any given point in time for the at least one two-dimensional array of detectors, the three-dimensional images being reconstructed by a method for resolving equations using the measurements, said process comprising: passing each of the collimating lines substantially over a helix centered on the axis; performing a conversion calculation stage of the parameterizing of the collimating lines, prior to the resolving of the equations, where each of the latter is assumed to be the origin of a virtual two-dimensional array of detectors focused onto a single focal point of the helix; and rotating the virtual array about the axis at a constant distance therefrom, the conversion calculations consisting of determining for each of the collimating lines of the virtual array, the position in the real array whereof it is the origin and the angular position of the real array about the axis, followed by a stage of regrouping the measurements in accordance with the determinations of the conversion calculations, so as to obtain virtual conical projections, the resolutions relating to the regrouping measurement.

2. Process for the reconstruction of three-dimensional images according to claim 1, characterized in that the method for resolving the measurements involves an inversion of the primary derivative of the Radon transform.

3. Process for the reconstruction of three-dimensional images according to claim 1, characterized in that the helical trajectory is a circular trajectory and the helix is a circle.

4. Process for the reconstruction of three-dimensional images according to claim 3, characterized in that all the focusing lines pass through a line tangential to the circle.

5. Process for the reconstruction of three-dimensional images according to claim 1, characterized in that the conversion calculations comprise three successive conversion states of virtual measurements according to three coordinates, each of said stages involving a linear interpolation.

* * * * *